(12) United States Patent
Bercovici et al.

(10) Patent No.: US 10,301,669 B2
(45) Date of Patent: *May 28, 2019

(54) DETECTION OF GENETIC SEQUENCES USING PNA PROBES AND ISOTACHOPHORESIS

(71) Applicant: TECHNION RESEARCH AND DEVELOPMENT FOUNDATION LIMITED, Haifa (IL)

(72) Inventors: Moran Bercovici, Haifa (IL); Nadya Ostromohov, Haifa (IL); Ortal Schwartz, Haifa (IL)

(73) Assignee: Technion Research and Development Foundation Limited, Haifa (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/469,724

(22) Filed: Mar. 27, 2017

(65) Prior Publication Data

US 2017/0198339 A1    Jul. 13, 2017

Related U.S. Application Data

(63) Continuation of application No. 14/461,645, filed on Aug. 18, 2014, now Pat. No. 9,683,960.

(30) Foreign Application Priority Data

Aug. 19, 2013    (IL) .......................... 228026

(51) Int. Cl.
*C12Q 1/6825*    (2018.01)
*G01N 27/447*    (2006.01)
*C12Q 1/6816*    (2018.01)

(52) U.S. Cl.
CPC ......... *C12Q 1/6825* (2013.01); *C12Q 1/6816* (2013.01); *G01N 27/4473* (2013.01); *G01N 27/44726* (2013.01); *G01N 27/44765* (2013.01); *G01N 27/44791* (2013.01)

(58) Field of Classification Search
CPC ..... C12Q 1/6816; G01N 27/447; C07H 21/04
See application file for complete search history.

(56) References Cited

U.S. PATENT DOCUMENTS 6,020,126 A      2/2000  Carlsson
2014/0014515 A1  1/2014  Santiago

OTHER PUBLICATIONS

Zhang et al.; Advantages of Peptide Nucleic Acids as Diagnostic Platforms for Detection of Nucleic Acids in Resourse Limited Settings, 2010, The Journal of Infectious Diseases, 201(S1), S42-S45.
Ostromohov et al. Leveraging Peptide Nucleic Acid Probes and Isotachophoresis for on-chip high sensitivity detection of DNA, 2013, 17th International Conference on Miniaturized Systems for Chemistry and Life Sciences Oct. 27-31, 2013, Freiburg, Germany, pp. 1-3.
Moran Bercovici et al: "Rapid hybridization of nucleic acids using isotachophoresis", Proceedings of the National Academy of Sciences of the United States of America, Jul. 10, 2012, vol. 109, No. 28, pp. 11127-11132 (6 pages).
Giancarlo Garcia-Schwarz et al: "On-chip Isotachophoresis for Separation of Ions and Purification of Nucleic Acids", Journal of Visualized Experiments, Mar. 2012, vol. 61, e3890 (8 pages).
V. N. Kondratova et al: "Isotachophoresis of Nucleic Acids in Agarose Gel Rods", Isotachophoresis of Nucleic Acids in Agarose Gel Rods, 2009, vol. 74, No. 11, pp. 1285-1288 (4 pages).
Thomas Hahn et al: "Microsystem for Isolation of Fetal DNA from Maternal Plasma by Preparative Size Separation", Clinical Chemistry, 2009, vol. 55, No. 12, pp. 2144-2152 (9 pages).
L.A. Marshall et al: "An injection molded microchip for nucleic acid purification from 25 microliter samples using sotachophoresis", Journal of Chromatography A, Feb. 2014, vol. 1331, pp. 139-142 (4 pages).
Douglas B. Cines et al: "The ITP syndrome: pathogenic and clinical diversity", Blood, Jun. 25, 2009, vol. 113, No. 26, pp. 6511-6521 (12 pages).
Moran Bercovici et al: "Rapid detection of urinary tract infections using isotachophoresis and molecular beacons", Analytical Chemistry, Jun. 2011, vol. 83, No. 11, pp. 4110-4117 (8 pages).
Zheng Li et al: "Characteristics of Peptide Nucleic Acid (PNA) and Application thereof in Molecular Biology Study", Biology Bulletin, Feb. 1999, vol. 34, No. 2, pp. 3-5 with English translation (11 pages).
Anita Rogacs et al: "Purification of nucleic acids using isotachophoresis", Journal of Chromatography A, Mar. 28, 2014, vol. 1335, pp. 105-120 (16 pages).

*Primary Examiner* — Narayan K Bhat
(74) *Attorney, Agent, or Firm* — Roach Brown McCarthy & Gruber, P.C.; Kevin D. McCarthy

(57) ABSTRACT

A method for sequence-specifically detecting a nucleic acid molecule. The method requires: a) contacting in an absence of an electric field, a mixture of nucleic acid molecules with a base pairing hybridizing molecule (BPHM) having a sequence of interest in a first solution and obtaining a hybrid consisting the nucleic acid molecule and the BPHM; b) introducing the first solution from step (a) into an ITP system, the ITP system comprises a second solution of high effective mobility leading electrolyte (LE) ions and a third solution of low effective mobility trailing electrolyte (TE); and c) applying the electric field across the second solution and the third solution. The hybrid focus at the sharp LE-TE interface in the ITP system. The TE has a higher mobility than the BPHM and the TE has a lower mobility than the hybrid. Sequence-specifically the detecting nucleic acid molecule by a signal from a label.

21 Claims, 5 Drawing Sheets

Specification includes a Sequence Listing.

DETECTION OF GENETIC SEQUENCES USING PNA PROBES AND ISOTACHOPHORESIS

FIELD OF INVENTION

This invention is directed to; inter alia, a system for sequence-specifically separating and/or identifying a nucleic acid molecule, comprising: a peptide nucleic acid (PNA) molecule; and an Isotachophoresis (ITP) separation system.

BACKGROUND OF THE INVENTION

Isotachophoresis ("ITP") is a variant of electrophoresis, characterized by the fact that separation is carried out in a discontinuous buffer system. Sample material to be separated is inserted between a "leading electrolyte" and a "terminating electrolyte" or mixed in any of these, the characteristic of these two buffers being that the leader has to have ions of net mobility higher than those of sample ions, while the terminator must have ions of net mobilities lower than those of sample ions. In such a system, sample components sort themselves according to decreasing mobilities from leader to terminator, in a complex pattern governed by the so-called Kohlrausch regulating function. The process has been described repeatedly, as for instance, Bier and Allgyer, Electrokinetic Separation Methods 443-69 (Elsevier/North-Holland 1979).

It is further characteristic of ITP that a steady state is eventually reached, where all components migrate at same velocity (hence the name) in sharply defined contiguous zones. Sample components can be separated in such a contiguous train of components by insertion of "spacers" with mobilities intermediary between those of the components one wishes to separate.

Isoelectric focusing ("IEF"), also sometimes called electrofocusing, is a powerful variant of electrophoresis. The principle of IEF is based on the fact that proteins and peptides, as well as most biomaterials, are amphoteric in nature, i.e., are positively charged in acid media and negatively charged in basic media. At a particular pH value, called the isoelectric point (PI), there is reversal of net charge polarity, the biomaterials acquiring zero net charge.

If such amphotcric materials are exposed to a d.c. current of proper polarity in a medium exhibiting a pH gradient, they will migrate, i.e., 'focus' toward the pH region of their PI, where they become virtually immobilized. Thus a stationary steady state is generated, where all components of the mixture have focused to their respective PIs.

The pH gradient is mostly generated 'naturally' i.e, through the electric current itself. Appropriate buffer systems have been developed for this purpose, containing amphoteric components which themselves focus to their respective PI values, thereby buffering the pH of the medium.

The two variants, IEF and ITP, differ in that IEF attains a stationary steady state whereas in ITP a migrating steady state is obtained. Thus, in IEF a finite length of migrating channel is always sufficient. In ITP, complete resolution may require longer migrating channels than is practical. In such case, the migrating components can be virtually immobilized by applying a counterflow, the rate of counterflow being matched to the rate of frontal migration of the sample ions. This is also known in the art.

IEF is most frequently carried out in polyacrylamide or agarose gels, where all fluid flow disturbances are minimized. ITP is most often carried out in capillaries. The sample is inserted at one end of the capillary, at the interface between leader and terminator, and the migration of separated components recorded by appropriate sensors at the other end of the capillary. Both such systems are used mainly for analytical or micro-preparative purposes.

ITP forms a sharp moving boundary between ions of like charge. The technique can be performed with anionic or cationic samples. The system quickly establishes a strong gradient in electric field at the ITP interface, due to the non-uniform conductivity profile. As per its name (from Greek, "isos" means "equal", "takhos" means "speed"), TE and LE ions travel at the same, uniform velocity, as a result of the non-uniform electric field and conservation of current (this is the so-called "ITP condition").

The ITP interface is self-sharpening: LE ions that diffuse into the TE zone experience a strong restoring flux and return to the leading zone (and vice versa for TE ions in the LE zone). Sample ions focus at this interface if their effective mobility in the TE zone is greater than those of the TE co-ions, and if their effective mobility in the LE zone is less than that of the LE co-ions. The self-sharpening and focusing properties of ITP contribute to the robustness of this technique and make ITP relatively insensitive to disturbances of the interface (e.g. due to pressure-driven flow or changes in geometry, such as contractions, expansions, and turns).

In peak mode ITP, sample ion concentrations are at all times significantly lower than LE and TE ion concentrations and therefore contribute negligibly to local conductivity. The distribution of sample ions is determined by the self-sharpening interface between neighboring zones (here the TE and LE) and the value of the sample effective mobility relative to these zones. Multiple sample ions focus within the same narrow ITP interface region as largely overlapping peaks.

SUMMARY OF THE INVENTION

In one embodiment, the present invention provides a system comprising: a peptide nucleic acid (PNA) molecule; a DNA molecule, an RNA molecule, or a combination thereof; and an Isotachophoresis (ITP) system. In some embodiments, the PNA molecule is labeled. In one embodiment, the label is a fluorescent label.

In a further embodiment, the present invention provides a method for sequence-specifically separating and/or detecting a nucleic acid molecule, comprising the steps of: contacting a mixture of nucleic acid molecules with a labeled peptide nucleic acid molecule (PNA) having an anti-sense sequence of interest in a first solution and obtaining a nucleic acid molecule/PNA hybrid; introducing the first solution between a fast leading electrolyte and a slow terminating electrolyte of an Isotachophoresis (ITP) system, the ITP system comprises a second solution of high effective mobility leading electrolyte (LE) ions and a third solution of low effective mobility trailing electrolyte (TE); applying voltage between the LE and the TE, inducing a low electrical field in the leading electrolyte and a high electrical field in the terminating electrolyte; wherein the nucleic acid molecule/PNA hybrid but not free PNA focus at the sharp LE-TE interface in the ITP system, thereby sequence-specifically separating and/or detecting a nucleic acid molecule.

In another embodiment, "sequence-specifically" is a contiguous nucleic acid sequence comprising at least 7 nucleotides. In another embodiment, "sequence-specifically" is a contiguous nucleic acid sequence comprising at least 10 nucleotides. In another embodiment, "sequence-specifically" is a contiguous nucleic acid sequence comprising or consisting 7 to 15,000 nucleotides. In another embodiment, "sequence-specifically" is a contiguous nucleic acid sequence comprising or consisting 10 to 10,000 nucleotides. In another embodiment, "sequence-specifically" is a contiguous nucleic acid sequence comprising or consisting 10 to 1,000 nucleotides. In another embodiment, "sequence-specifically" is a contiguous nucleic acid sequence comprising or consisting 10 to 500 nucleotides.

In a further embodiment, the present invention provides a kit comprising a peptide nucleic acid molecule (PNA) having a sequence of interest, a solution for selectively hybridizing a nucleic acid molecule and said PNA; a solution having high effective mobility leading electrolyte (LE); a solution having low effective mobility trailing electrolyte (TE); and instructions for separating and/or detecting a hybrid consisting the nucleic acid molecule and the PNA.

DETAILED DESCRIPTION OF THE INVENTION

Figure 1:
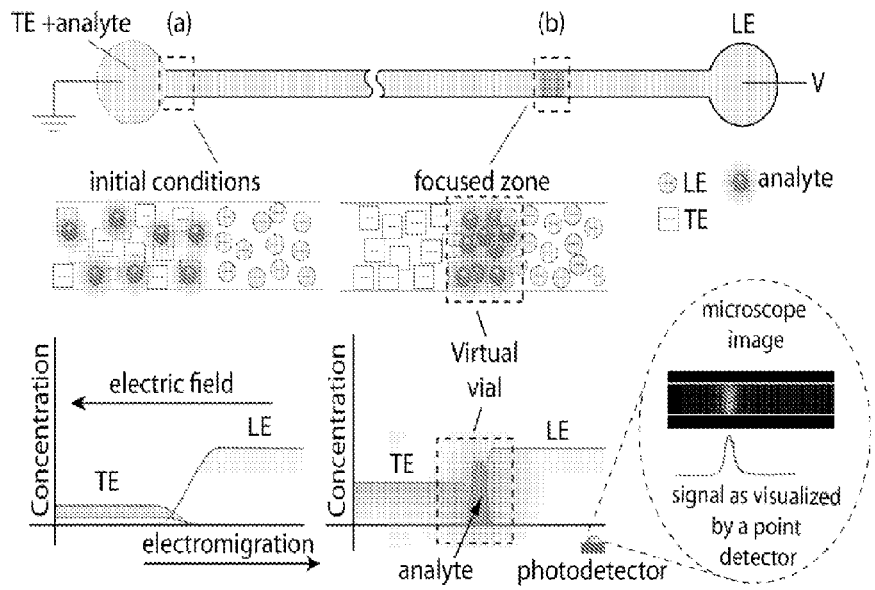
FIG. 1. A schematic of a typical ITP assay. A simple microchannel is connected to two reservoirs and is initially filled with LE solution. (a) Analytes are mixed in the trailing electrolyte (TE) reservoir. (b) When an electric field is applied all ions electromigrate in the channel. The LE and TE are chosen such that analytes of interest have a higher mobility than the TE, but cannot over-speed the LE. This results in selective focusing at the sharp LE-TE interface FIG. 2. Schematic illustration of the assay. (a) A microfluidic channel connecting two reservoirs is initially filled with LE. The left reservoir is filled with a mixture of TE, DNA sample and PNA probes. (b) In a control case, when an electric field is applied across the channel no targets are available to carry the probes into the channel, and all the probes remain in the reservoir. (c) In the presence of target, PNA probes rapidly bind to any matching DNA sequences. The negatively charged DNA and PNA-DNA hybrids electromigrate into the channel and focus at the ITP interface, while unbound, weakly charged PNA probes remain in the reservoir.

In one embodiment, the present invention provides a system comprising: (A) a peptide nucleic acid (PNA) molecule; (B) a nucleic acid molecule; and (C) an Isotachophoresis (ITP) system. In another embodiment, an ITP system comprises: a first zone comprising a solution of high effective mobility leading electrolyte (LE) ions; a second zone comprising a solution of low effective mobility trailing electrolyte (TE); and an anode and a cathode.

In another embodiment, the nucleic acid molecule is DNA, RNA, miRNA, mRNA, tRNA, or rRNA. In another embodiment, the leading electrolyte (LE) buffer is chosen such that its anions have higher effective electrophoretic mobility than the anions of the trailing electrolyte (TE) buffer (Effective mobility describes the observable drift velocity of an ion and takes into account the ionization state of the ion, as described in detail by Persat et al.). In another embodiment, sample ions of intermediate effective mobility race ahead of TE ions but cannot overtake LE ions, and so they focus at the LE-TE interface (hereinafter called the "ITP interface"). In another embodiment, the LE and TE buffers are chosen such that nucleic acid molecule of interest (to be detected or separated) have a higher mobility than the TE, but cannot over-speed the LE. In another embodiment, the TE and LE buffers form regions of respectively low and high conductivity, which establish a steep electric field gradient at the ITP interface. In another embodiment, the LE buffer (or LE) has a high ionic strength. In another embodiment, $Mg^{2+}$ ions are used as a counter ion to promote rapid hybridization. In another embodiment, TE buffer (or TE) comprises MES (2-(N-morpholino)ethanesulfonic acid). In another embodiment, LE comprises hydrochloric acid. In another embodiment, LE comprises 70 to 150 mM HCl and 150 to 280 mM Bistris (2,2-Bis(hydroxymethyl)-2,2',2"-nitrilotriethanol).

In another embodiment, TE has a higher mobility than the unbound PNA probe. In another embodiment, TE has a lower mobility than the nucleic acid molecule/PNA hybrid. In another embodiment, LE has a higher mobility than the nucleic acid molecule/PNA hybrid. In another embodiment, LE has a higher mobility than the nucleic acid molecule/PNA hybrid, the nucleic acid molecule/PNA hybrid has a higher mobility than TE, and TE has a higher mobility than the unbound PNA molecule.

In another embodiment, LE comprises hydrochloric acid. In another embodiment, LE comprises 70 to 100 mM HCl. In another embodiment, LE comprises hydrochloric acid. In another embodiment, LE comprises 100 to 150 mM HCl. In another embodiment, LE comprises hydrochloric acid. In another embodiment, LE comprises 120 to 150 mM HCl. In another embodiment, LE comprises hydrochloric acid. In another embodiment, LE comprises 150 to 200 mM Bistris. In another embodiment, LE comprises 200 to 250 mM Bistris. In another embodiment, LE comprises 150 to 200 mM Bistris. 220 to 280 mM Bistris.

In another embodiment, in peak mode ITP with sample mixed in the TE reservoir, the amount of accumulated sample at the ITP interface, $N_a$, is determined by the ratio of the electrophoretic mobility of the analyte, $\mu_a$, and of the TE, $\mu_{TE}$, $$N_a \sim \frac{\mu_a}{\mu_{TE}} - 1.$$

In another embodiment, tricine with bistris is utilized as the TE buffer yielding a trailing ion mobility of $5.68 \cdot 10^{-9}$ $[m^2 V^{-1} s^{-1}]$. In another embodiment, the mobility of TE is lower than the mobility of the nucleic acid molecule of the invention. In another embodiment, PNA molecule has a neutral or slight positive charge. In another embodiment, selective focusing of PNA-nucleic-acid-molecule complexes, but not free PNA requires specific choice of an ITP system comprised of a TE buffer with sufficient mobility to over-speed the free PNA probes but not the PNA-nucleic-acid-molecule complexes ($\mu_{PNA} < \mu_{TE} < \mu_{complex}$).

In another embodiment, according to the system, kits and methods of the invention no signal for the free PNA molecule is obtained while maintaining a significant signal when nucleic acid molecule complexes, are present.

In another embodiment, ITP includes a microchannel connected to two reservoirs and is initially filled with LE solution. In another embodiment, a sample comprising a nucleic acid molecule to be detected is mixed in the trailing electrolyte (TE) reservoir. In another embodiment, a sample comprising a nucleic acid molecule to be detected is mixed in the leading electrolyte (LE) reservoir. In another embodiment, an electric field induces the electromigration of all ions in the channel.

In another embodiment, peptide nucleic acid (PNA) is an artificial DNA analogue in which the natural negatively charged deoxyribose phosphate backbone has been replaced by a synthetic neutral pseudo peptide backbone. In another embodiment, the four natural nucleobases are retained on the backbone at equal spacing to the DNA bases. In another embodiment, PNA is substituted with another molecule which hybridizes according to base pairing (biologically stable molecule capable of sequence specific binding to DNA and RNA) with a nucleic acid molecule and renders the hybridized nucleic acid molecule weakly charged or uncharged. In another embodiment, the present invention takes advantage of PNA's hybridization properties and specificity, and utilizes PNA as a highly selective biosensor for nucleic acid sequence detection.

In another embodiment, PNA comprise the formula:

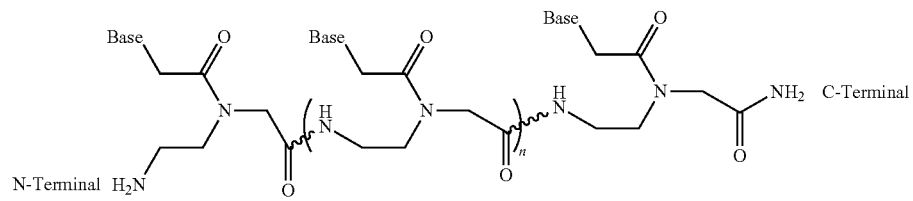

In another embodiment, a PNA molecule as described herein comprises at least one lysine residue. In another embodiment, a PNA molecule as described herein is further modified with at least one lysine residue. In another embodiment the concentration of PNA is from 1 nM to 120 µM. In another embodiment the concentration of PNA is from 2 nM to 500 nM. In another embodiment the concentration of PNA is from 500 nM to 2 µM. In another embodiment the concentration of PNA is from 2 µM to 30 µM.

In another embodiment, n equals 7 to 15,000. In another embodiment, n equals 10 to 10,000. In another embodiment, n equals 20 to 35,000. In another embodiment, n equals 10 to 1,000.

In another embodiment, PNA comprise primary amine at the N-terminal. In another embodiment, PNA further comprises a label. In another embodiment, the N-terminal primary amine of the PNA is labeled. In another embodiment, PNA is used as a probe.

In another embodiment, labeled PNA is a PNA molecule labeled with a positively charged molecule. In another embodiment, labeled PNA is a PNA molecule labeled with a cationic marker. In another embodiment, labeled PNA comprises a fluorescent label. In another embodiment, labeled PNA comprises a radioactive label. In another embodiment, labeled PNA comprises a chemiluminescent label. In another embodiment, labeled PNA comprises a colorimetric label. In another embodiment, PNA serves as a probe, as an electrical charge quencher, as a specific antisense molecule for the identification and/or separation of a nucleic acid molecule having a specific sequence of interest (the target nucleic acid molecule).

In another embodiment, a system as described herein further comprises a photodetector. In another embodiment, a system as described herein further comprises a photomultiplier tube (PMT). In another embodiment, a system as described herein further comprises a camera. In another embodiment, a system as described herein further comprises a radioactive probe or detector. In another embodiment, a system as described herein further comprises a calorimetric detector.

In another embodiment, a system and a method as described herein detects specific DNA fragments in a sample. In another embodiment, a system and a method as described herein detect specific DNA fragments at a concentration of at least 100 fM (in a sample). In another embodiment, a system and a method as described herein detect specific DNA fragments at a concentration of at least 50 fM (in a sample). In another embodiment, a system and a method as described herein detect specific DNA fragments at a concentration of at least 75 fM (in a sample). In another embodiment, a system and a method as described herein detect specific DNA fragments at a concentration of at least 200 fM (in a sample). In another embodiment, a system and a method as described herein detect specific DNA fragments at a concentration of at least 500 fM (in a sample). In another embodiment, a system and a method as described herein detect as little as 75 fM of specific DNA fragments in a sample. In another embodiment, a system and a method as described herein detect as little as 100 fM of specific DNA fragments in a sample. In another embodiment, a system and a method as described herein detect as little as 200 fM of specific DNA fragments in a sample. In another embodiment, a system and a method as described herein detect as little as 500 fM of specific DNA fragments in a sample.

In another embodiment, a system and a method as described herein demonstrate 5 orders of magnitude dynamic range. In another embodiment, a system and a method as described herein demonstrate 2-8 orders of magnitude dynamic range. In another embodiment, a system and a method as described herein demonstrate 3-10 orders of magnitude dynamic range.

In another embodiment, the present invention provides an ITP kit comprising a PNA molecule for probing a nucleic acid molecule having a specific sequence of interest and specific instructions for preparing a TE buffer and a LE buffer. In another embodiment, the present invention provides an ITP kit comprising a system of the invention. In another embodiment, the present invention provides a kit comprising an instruction manual describing the method and/or system disclosed herein.

In another embodiment, probing is sequence specific probing utilizing at least one PNA molecule as described herein. In another embodiment, probing is probing a sequence as short as 7 contiguous nucleic acid residues (such as DNA or RNA). In another embodiment, probing is probing a sequence comprising at least 7 contiguous nucleic acid residues (such as DNA or RNA). In another embodiment, probing is sequence specific probing. In another embodiment, probing is probing a sequence comprising 10 or more contiguous nucleic acid residues. In another embodiment, probing is sequence specific probing. In another embodiment, probing is probing at least a sequence consisting 10 to 1000 contiguous nucleic acid residues. In another embodiment, probing is probing at least a sequence consisting 10 to 500 contiguous nucleic acid residues. In another embodiment, probing is also a measure of the number "n" provided in the PNA formula.

In another embodiment, the present invention provides a kit for carrying out ITP separation of nucleic acid analytes/targets in a sample. According to some embodiments of the present invention, wherein the kit comprises LE buffer, TE buffer, and a PNA molecule for sequence specific identification and/or isolation of a nucleic acid molecule of interest.

In another embodiment, the present invention provides a kit as described herein further comprising an electrophoresis apparatus. In another embodiment, the present invention provides a kit as described herein further comprising an electrophoresis apparatus coupled to a central processing unit (CPU) that may operate the electrophoresis apparatus based on a predetermined set of instructions. In another embodiment, the present invention provides a kit further comprising the target nucleic acid as a positive control. In another embodiment, the present invention provides a kit further comprising a negative control comprising a sequence having at least a single nucleic acid addition, deletion, or substitution compared to the target nucleic acid molecule.

In another embodiment, the invention further provides a method for sequence-specifically detecting a nucleic acid molecule, using the system of claim 1 and comprising the steps of: (a) introducing the PNA probe with nucleic acid sample into the said TE solution, obtaining a nucleic acid molecule/PNA hybrid; applying electrical field between said LE and TE zones such that said nucleic acid molecule/PNA hybrid but not free PNA focus at the sharp LE-TE interface enabling detection of the nucleic acid molecule/PNA hybrid; (b) injecting a finite volume of a mixture composed of a nucleic acid molecule/PNA hybrid between said TE and LE; applying electrical field between said LE and TE zones such that said nucleic acid molecule/PNA hybrid but not free PNA focus at the sharp LE-TE interface enabling detection of the nucleic acid molecule/PNA hybrid; (c) injecting a finite volume of a mixture composed of PNA probes into the said LE solution and the nucleic acid sample into the said TE solution; applying electrical field between said LE and TE zones such that a high concentration zone of nucleic acid molecule/PNA hybrid is formed at the sharp LE-TE interface enabling detection of the nucleic acid molecule/PNA hybrid.

In another embodiment, a method for separating and/or isolating a nucleic acid molecule of interest, the PNA, or the hybrid consisting the PNA/nucleic acid molecule of interest, further comprises subjecting the ITP focused composition which comprises free nucleic acid molecules and hybrids of PNA/nucleic acid molecule (but free of unhybridized PNAs) to a second step that actually separates and/or isolates the nucleic acid molecule of interest and/or the hybrid comprising PNA/nucleic acid molecule of interest. In another embodiment, the second step includes subjecting the composition which comprises free nucleic acid molecules and hybrids of PNA/nucleic acid molecule to an electric field and separating the hybrid according to its isoelectric point. In another embodiment, the second step includes subjecting the composition which comprises free nucleic acid molecules and hybrids of PNA/nucleic acid molecule to a separating column which is capable of separating/distinguishing free nucleic acid molecules from hybrids of the invention. In another embodiment, an electric field is applied across the ITP solutions or buffers. In another embodiment, an electric field is applied across the TE and LE solutions/buffers.

In another embodiment, a third step of separating the nucleic acid of interest from the PNA is applied. In another embodiment, the third step includes subjecting the hybrid to urea or any other solution capable of separating the PNA-nucleic acid molecule. In another embodiment, a fourth step of discarding the PNA is applied. In another embodiment, methods of isolating a PNA or a nucleic acid molecule from a solution that comprises both PNA and a nucleic acid molecule are known to one of skill in the art. In another embodiment, the methods of the present invention result in separating, isolating and/or enriching the nucleic acid molecule of interest or the PNA.

In another embodiment, the invention further provides a method for sequence-specifically separating or isolating a nucleic acid molecule, comprising the steps of: (a) contacting a mixture of nucleic acid molecules with a labeled peptide nucleic acid molecule (PNA) having a sequence of interest in a first solution and obtaining a nucleic acid molecule/PNA hybrid (sense-anti-sense complex); (b) introducing the first solution between a fast leading electrolyte and a slow terminating electrolyte of an isotachophoresis (ITP) system, the ITP system comprises a second solution of high effective mobility leading electrolyte (LE) ions and a third solution of low effective mobility trailing electrolyte (TE); and (c) applying a low electrical field in the leading electrolyte and a high electrical field in the terminating electrolyte; wherein the nucleic acid molecule/PNA hybrid but not free PNA focus at the sharp LE-TE interface in the ITP system, thereby sequence-specifically separating a nucleic acid molecule. In another embodiment, the first solution has an ionic strength that enables stringent hybridization conditions between the PNA and the target nucleic acid molecule. In another embodiment, a person of ordinary skill in the art can readily prepare a solution that enables stringent hybridization conditions as described herein. In another embodiment, the nucleic acid molecule is 10-100 nucleotides long and the PNA molecule renders the hybrid positively charged. In another embodiment, the nucleic acid molecule is 10-50 nucleotides long and the PNA molecule renders the hybrid positively charged (wherein the unhybridized nucleic acid molecules are negatively charged).

In another embodiment, PNA having a sequence of interest is a PNA directed against a particular sequence of DNA or RNA. In another embodiment, PNA having a sequence of interest is a PNA that will bind only a DNA or a RNA molecule comprising the sequence of interest to which the PNA molecule is designed a hybridize to. In another embodiment, PNA having a sequence of interest is a PNA that is a complete and perfect antisense to a particular sequence of DNA or RNA.

In another embodiment, the phrase "sequence-specifically separating" includes the phrase "sequence-specifically identifying". In another embodiment, a PNA probe as described herein is further labeled as described hereinabove. In another embodiment, the term "isolating" is substituted with the term "enriching". In another embodiment, separating is discarding the free unhybridized PNA.

In another embodiment, the present invention provides methods, systems and kits that reduce false positive or false negative results. In another embodiment, the present invention provides methods, systems and kits that reduce background noise. In another embodiment, the present invention provides methods, systems and kits that reduce background originating from a free PNA molecule or false identification of the target nucleic acid molecule. In another embodiment, the present invention provides methods, systems and kits that provide accurate quantitative measures of the nucleic acid molecule of interest. In another embodiment, the present invention provides methods, systems and kits that provide an efficient separating technique for a nucleic acid molecule of interest. In another embodiment, the present invention provides methods wherein the free, unhybridized, PNAs aren't focused in the interface. In another embodiment, free PNAs aren't focused in the interface. In another embodiment, the method and system of the invention includes at least one detection unit for detecting the label of the PNA probe. In another embodiment, detection units for detecting different labels are known to one of average skill in the art. In another embodiment, detection units for detecting different labels are described hereinabove.

In another embodiment, the label is Acridine orange. In another embodiment, the label is Acridine yellow. In another embodiment, the label is Alexa Fluor. In another embodiment, the label is 7-Aminoactinomycin D. In another embodiment, the label is 8-Anilinonaphthalene-1-sulfonic acid. In another embodiment, the label is an ATTO dye. In another embodiment, the label is Auramine-rhodamine stain. In another embodiment, the label is Benzanthrone. In another embodiment, the label is Bimane. In another embodiment, the label is 9,10-Bis(phenylethynyl)anthracene. In another embodiment, the label is 5,12-Bis(phenylethynyl)naphthacene. In another embodiment, the label is Bisbenzimide. In another embodiment, the label is a Blacklight paint. In another embodiment, the label is Brainbow. In another embodiment, the label is Calcein. In another embodiment, the label is Carboxyfluorescein. In another embodiment, the label is Carboxyfluorescein diacetate succinimidyl ester. In another embodiment, the label is Carboxyfluorescein succinimidyl ester. In another embodiment, the label is 1-Chloro-9,10-bis(phenylethynyl)anthracene. In another embodiment, the label is 2-Chloro-9,10-bis(phenylethynyl)anthracene. In another embodiment, the label is 2-Chloro-9,10-diphenylanthracene. In another embodiment, the label is Coumarin. In another embodiment, the label is DAPI. In another embodiment, the label is a Dark quencher. In another embodiment, the label is DiOC6. In another embodiment, the label is DyLight Fluor. In another embodiment, the label is Ethidium bromide. In another embodiment, the label is Fluo-3. In another embodiment, the label is Fluo-4. In another embodiment, the label is a FluoProbe. In another embodiment, the label is Fluorescein. In another embodiment, the label is Fluorescein isothiocyanate. In another embodiment, the label is a Fluoro-Jade stain. In another embodiment, the label is Fura-2. In another embodiment, the label is Fura-2-acetoxymethyl ester. In another embodiment, the label is GelGreen. In another embodiment, the label is GelRed. In another embodiment, the label is Green fluorescent protein. In another embodiment, the label is a Heptamethine dye. In another embodiment, the label is Hoechst stain. In another embodiment, the label is Indian yellow. In another embodiment, the label is Indo-1. In another embodiment, the label is Lucifer yellow. In another embodiment, the label is Luciferin. In another embodiment, the label is MCherry. In another embodiment, the label is Merocyanine. In another embodiment, the label is Nile blue. In another embodiment, the label is Nile red. In another embodiment, the label is an Optical brightener. In another embodiment, the label is Perylene. In another embodiment, the label is Phloxine. In another embodiment, the label is P cont. In another embodiment, the label is Phycobilin. In another embodiment, the label is Phycoerythrin. In another embodiment, the label is Phycoerythrobilin. In another embodiment, the label is Propidium iodide. In another embodiment, the label is Pyranine. In another embodiment, the label is a Rhodamine. In another embodiment, the label is RiboGreen. In another embodiment, the label is RoGFP. In another embodiment, the label is Rubrene. In another embodiment, the label is (E)-Stilbene. In another embodiment, the label is (Z)-Stilbene. In another embodiment, the label is a Sulforhodamine. In another embodiment, the label is SYBR Green I. In another embodiment, the label is Synapto-pHluorin. In another embodiment, the label is Tetraphenyl butadiene. In another embodiment, the label is Tetrasodium tris(bathophenanthroline disulfonate)ruthenium(II). In another embodiment, the label is Texas Red. In another embodiment, the label is Titan yellow. In another embodiment, the label is TSQ. In another embodiment, the label is Umbelliferone. In another embodiment, the label is Yellow fluorescent protein. In another embodiment, the label is YOYO-1. In another embodiment, the label is a chemiluminescent dye. In another embodiment, the label is a radioisotope or a radioactive dye. In another embodiment, the label is a dye that can be detected by a naked eye.

In another embodiment, the nucleic acid molecule which is the target sequence to be detected by specific hybridization comprises 7 to 10000 bases. In another embodiment, the nucleic acid molecule which is the target sequence to be detected comprises 10 to 10000 bases. In another embodiment, the nucleic acid molecule which is the target sequence to be detected comprises 10 to 1000 bases. In another embodiment, the nucleic acid molecule which is the target sequence to be detected comprises 10 to 500 bases. In another embodiment, the nucleic acid molecule which is the target sequence to be detected comprises 20 to 400 bases. In another embodiment, the nucleic acid molecule which is the target sequence to be detected comprises 50 to 500 bases. In another embodiment, the nucleic acid molecule which is the target sequence to be detected comprises 100 to 10000 bases. In another embodiment, the nucleic acid molecule which is the target sequence to be detected comprises 500 to 5000 bases.

In another embodiment, the nucleic acid molecule/PNA hybrid has a higher mobility than the TE. In another embodiment, the nucleic acid molecule/PNA hybrid has a lower mobility than the LE. In another embodiment, the TE has a higher mobility than the free PNA probe. In another embodiment, the TE has a lower mobility than the nucleic acid molecule/PNA hybrid. In another embodiment, the TE has a lower mobility than the nucleic acid molecule.

In another embodiment, the first solution comprises TE. In another embodiment, the first solution comprises LE.

In another embodiment, labeled PNA comprises a single sequence of PNA directed against one specific nucleic acid sequence. In another embodiment, labeled PNA comprises multiple sequences of PNAs directed against multiple nucleic acid sequences wherein each PNA is labeled with a different molecule or dye. In another embodiment, each PNA (having a specific sequence) is designed to induce a specific charge on the hybrid thus each hybrid is distinguishable according to its unique electrical charge.

In another embodiment, the term "hybrid" is defined as a complex of PNA with DNA, RNA, or a molecule comprising both DNA and RNA bases. In another embodiment, "hybrid" is defined as a complex depending on base pairing.

In another embodiment, the target nucleic acid molecule to be probed and PNA are mixed with the LE and/or the TE. In another embodiment, the effective mobility of the "hybrid" (the bound heterocomplex) and the effective mobility of PNA differ.

In another embodiment, bound complex/hybrid k translocated to and/or extracted from ITP focus zone. In another embodiment, analysis of the bound complex is further performed in the ITP zone of the hybrid.

In another embodiment, the method of the present invention can be utilized to identify a nucleic acid molecule of interest such as a nucleic acid molecule that identifies a pathogen. In another embodiment, the method of the present invention can be utilized to identify a nucleic acid molecule of interest such as a gene of interest or a regulatory element of interest. In another embodiment, the method of the present invention can be utilized for screening an infection by obtaining a patient specimen (e.g., urine sample, blood sample etc.), and performing the above described methods and analyses, where the ITP sample is derived from the patient specimen, and the PNA is capable of binding to the target nucleic acid molecule which is a marker for disease. In another embodiment, nucleic acid molecules that can serve as markers for disease include bacterial nucleotide sequences, viral RNA or DNA sequences, mitochondrial DNA sequences, micro RNA sequences, or messenger RNA sequences that encode host or pathogen proteins involved in disease, etc.

In another embodiment, the present method requires minimal sample preparation and performs extraction, focusing, and detection of a target nucleic acid molecule in a single step.

In another embodiment, the theory behind ITP is provided in Bahga S S, Kaigala G V, Bercovici M, Santiago J G. High-sensitivity detection using isotachophoresis with variable cross-section geometry. Electrophoresis. 2011 February; 32(5):563-72; Khurana T K, Santiago J G. Sample zone dynamics in peak mode isotachophoresis. Anal Chem. 2008 Aug. 15; 80(16):6300-7; and Isotachophoresis: Theory, Instrumentation and Applications. F. M. Everaerts; J. L. Beckers, T. P. E. M. Verheggen, Elsevier, Sep. 22, 2011, which are hereby incorporated by reference in their entirety.

In another embodiment, ITP is performed in a peak mode. In another embodiment, ITP is performed in a plateau mode. In another embodiment, "Plateau mode" refers to a wide sample-zone compared to the transition zones, i.e. the sample concentration distribution forms a plateau with blurred boundaries towards LE and TE. In another embodiment, "Peak mode" refers to a very short sample zone, where the two transition zones at both sides of the sample overlap or when the sample is entirely within the interface between LE and TE. In another embodiment, a sample comprises a hybrid composed of PNA and a nucleic acid molecule.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells——A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Strategies for Protein Purification and Characterization—A Laboratory Course Manual" CSHL Press (1996); all of which are incorporated by reference. Other general references are provided throughout this document.

Materials and Methods

An ITP system such as illustrated in FIG. 1 was used for the current experiments. The system included a simple microchannel connected to two reservoirs that were initially filled with LE solution. (a) Analytes (the target DNA sequences) were mixed in the trailing electrolyte (TE) reservoir. (b) When an electric field was applied all ions electromigrate in the channel. The LE and TE were chosen such that analytes of interest had a higher mobility than the TE, but cannot over-speed—the LE. These settings result in selective focusing at the sharp LE-TE interface.

Study Design

Figure 2:
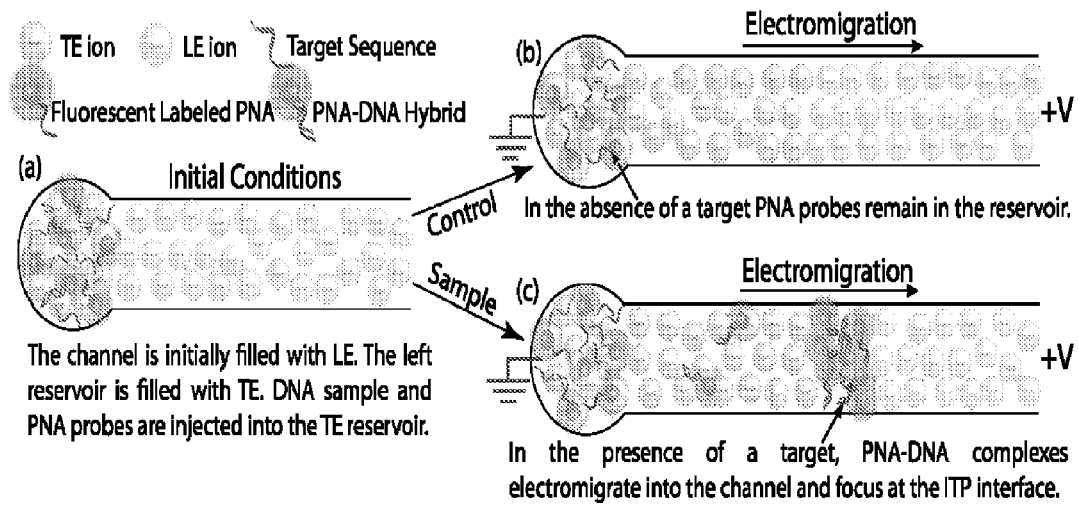

TAMRA labeled PNA TAMRA-OO-ATTCGTTG-GAAACGGGA (SEQ ID NO: 1) were utilized to serve as sequence-specific probes. The probes were then mixed with sample (containing target nucleic acid sequence of interest) in the TE reservoir of an anionic ITP setup (FIG. 2). FIG. 2 presents a schematic illustration of the assay. The sample was injected and an excess amount of PNA probes into the TE reservoir of an anionic ITP setup, allowing probes to rapidly bind to any matching target sequences present. The buffer system is chosen such that the electrophoretic mobility of the TE is higher than that of the free (unhybridized) probes but lower than that of the PNA-DNA hybrids. Therefore, once an electric field is applied, excess (unbound) PNA probes remain in the reservoir, while the negatively charged PNA-DNA hybrids electromigrate and focus at the ITP interface, resulting in a fluorescent signal. Hence, a fluorescent signal is obtained only in the presence of the target sequences "carrying" the otherwise neutral PNA probes to the interface. This allowed a highly sensitive, direct detection of target nucleic acids while completely eliminating background noise associated with unbound probes.

An excess concentration of probes was used such that the probe rapidly bind to any matching DNA or RNA sequences present in the sample/reservoir, creating PNA-DNA or PNA-RNA hybrids.

Once an electric field was applied, the negatively charged hybrids electromigrated in the direction of the positive electrode and focus at the ITP interface, resulting in a fluorescent signal. Since the free (unhybridized) PNA probes were uncharged (or weakly charged), excess (unbound) PNA probes did not migrate in an electric field. Hence, a fluorescent signal was obtained only in the presence of the target sequences "carrying" the otherwise neutral PNA probes to the interface. This enabled direct detection of target nucleic acid molecules, while essentially eliminating background noise due to unhybridized probes.

It is important to emphasize that the accuracy and the actual elimination of noise were accomplished due to the novel use of a peptide nucleic acid molecule probe which does not focus under ITP, unless hybridized to its target. This design of an ITP system (specific chemistry) under which free PNA probes do not focus, but PNA-target hybrids do focus had tremendous advantages over the state of the art. For example the current experiments demonstrate the ability to accurately isolate and/or detect, in free solution, substantially any length of DNA or RNA target with PNA probes. As mentioned hereinabove the present settings are based on a method for detection of nucleic acid molecules using a 'slower than DNA' or 'faster than DNA' probe.

PNA and Target Nucleic Acid Molecules

TAMRA (Carboxytetramethylrhodamine)-labeled PNA probes (5'-TAMRA-OO-ATTCGTTGGAAACGGGA-3' (SEQ ID NO: 1) sequence, was synthesized by Bio-Synthesis, Lewisville, Tex., USA). TAMRA is a cationic dye which has a single positive charge, and thus it is expected that it will impart an overall positive charge on the PNA probes. In practice, a weak negative charge was recorded at pH ~pH 6.5.

A 35 bp long target (5'-TTCGACGCTTCCCGTTTC-CAACGAATACTTAGGTT-3', SEQ ID NO: 2)) was used as target nucleic acid molecule. —A 17 nt long target (5'-TCCCGTTTCCAACGAAT-3') (SEQ ID NO: 3). —A 78 nt long target (5'-TTCGACGCTTCGACGCTTCGACGCT-TCCCGTTTCCAACGAA TACTTAGGTTACTTAGGT-TACTTAGGTTACTTAGGTT-3') (SEQ ID NO: 4).

Solutions 100 mM or 200 mM HCl (hydrochloric acid) as a leading ion, and 200 mM or 400 mM Bistris (2,2-Bis(hydroxymethyl)-2,2',2"-nitrilotriethanol) as the counterion were utilized. To enable focusing of PNA-DNA hybrids, while not focusing free PNA probes, MES (2-(N-morpholino)ethanesulfonic acid) was used as the trailing ion. LE included 100 mM HCl and 200 mM bistris. TE included 10 mM MES, and 20 mM bistris.

Example 1

PNA Based ITP Detection and Quantification

The present experiment demonstrated the feasibility of the test and its ability to identify and quantify the amount of initial target concentration. A notable advantage of the present invention became apparent as an extremely high initial probe concentration of 8 µM—the control case registered no signal. Importantly, it was shown that the present assay is capable detecting sequences as short as 17 bp/nt. This is in contrast to sieving-matrix based separations, which are limited to the detection of much longer sequences.

Figure 3:
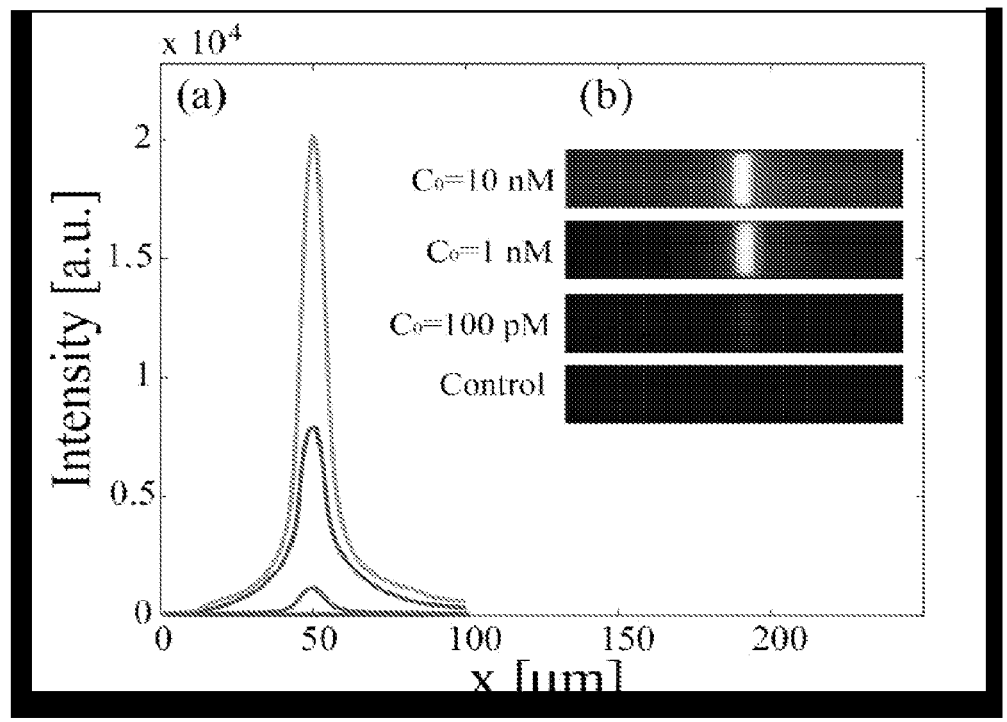
FIG. 3. Is a graph accompanied by micrograph of the target band which demonstrate DNA detection using fluorescently labeled PNA probes. (a) Area averaged intensity profiles of the fluorescent signal registered 7 mm from the TE reservoir. A fixed concentration of 8 µM of PNA probes was injected into the TE, and vary the range of DNA targets between 100 pM and 10 nM. In the control case no targets were added to the reservoir. (b) Raw intensity images corresponding to each concentration. LE is 100 mM HCl and 200 mM bistris. TE is 10 mM MES, and 20 mM bistris.

As shown in FIG. 3 the DNA target was detected by using fluorescently labeled PNA probes. The area averaged intensity profiles of the fluorescent signal registered 7 mm from the TE reservoir. A fixed concentration of 8 µM of PNA probes was mixed with the TE, and various DNA. targets concentrations between 100 pM and 10 nM were utilized. In the control case no targets were added to the reservoir. The results accurately mirror the actual corresponding concentration that was used for each test. Thus the present invention provides the benefit of accurately separating and quantifying a target nucleic acid molecule of interest.

Figure 4:
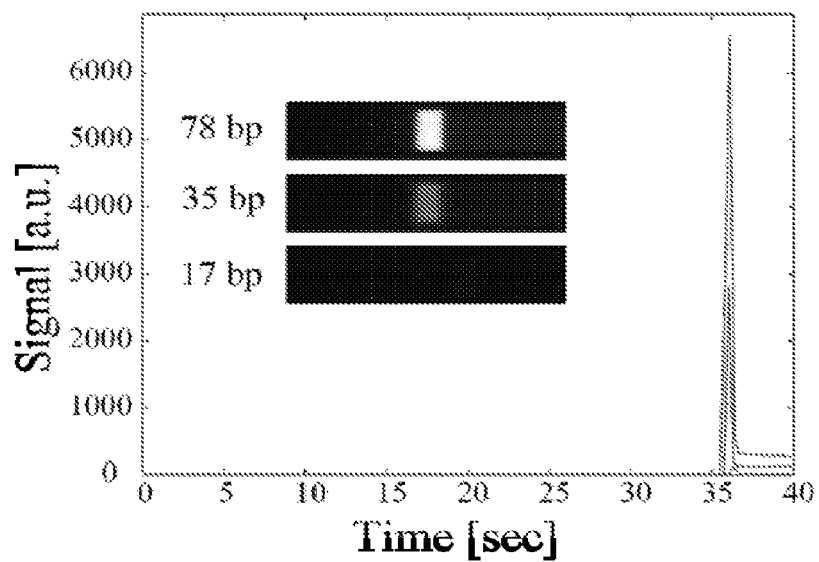
FIG. 4. Is a graph accompanied by micrograph of the target band demonstrating the applicability of the assay for detection of DNA targets between 17 and 78 bp in length. Even targets as short as 17 bp result in sufficiently charged complexes which focus under ITP. However, as the length of the target increases, so does the electrophoretic mobility of the probe-target complex. This results in a higher influx into the ITP interface and thus higher signals for longer targets. For targets longer than 200 bp, this is expected to stop, as the mobility of free DNA reaches a constant value.

As shown in FIG. 4 the present invention is applicable for detecting DNA targets of varying lengths (17, 35 and 78 bp in length). Even targets as short as 17 bp resulted in sufficiently charged complexes which focus under ITP. However, as the length of the target increases, so does the electrophoretic mobility of the probe-target complex. This resulted in a higher inflx into the ITP interface and thus higher signals for longer targets. For targets longer than 200 bp, it is expected to stop, as the mobility of free DNA reaches a constant value.

The current method can include the mixing of the PNA probe in with LE, TE, or both. The PNA probe can be designed to be positively charged (e.g. by adding lysine groups), in which case the liberty to choose any ITP system grows. PNA-DNA hybridization could take place either in one of the reservoirs, or at the ITP interface. Hybridization at the interface could be performed in several ways:

Placing a finite volume of positively charged PNA probe in the LE, such that it serves as a counterion and electromigrates in the opposite direction to ITP. Only PNA probes hybridized with the DNA would remain at the interface, while the rest would migrate toward the TE.

Placing a weakly negative PNA probe (having a lower mobility than the TE) in the LE. The ITP interface containing focused DNA would thus move through the PNA concentration, and retain at the interface only PNA-DNA hybrids.

Using a weakly charged PNA probe, a two-step method could be performed: initially a low mobility TE is used such that the PNA and DNA both focus and hybridize together at the interface. After sufficient hybridization time, an intermediate mobility spacer (with a higher mobility than the PNA, but lower mobility than the hybrids) is used to separate the two.

The method was also performed while utilizing counterflow to hold the interface stationary. This allows, for example, using initially an LE containing PNA probes for hybridization, and subsequently switching to a "clean" LE to remove any background noise.

Likewise, the method could be multiplexed by using multiple probes, each labeled with a different florescent molecule, or labeled with quantum dots or multiplexed by using multiple parallel channels, each containing a different PNA probe (which could all be labeled with the same fluorophore).

Last, the method could be used to detect and separate different DNA sequences by chemically altering the PNA probes to have different charges.

Example 2

PNA Probes

Two types of PNA probes were utilized in these experiments. For the sensitivity and specificity experiments that were designed a 14-mer PNA probe, complementary to a section of 16S rRNA of E. coli, (36, 37), Cy5-Lys-O-CGTCAATGAGCAAA-Lys (SEQ ID NO: 5), synthesized by Panagene (Daejeon, Korea). In order to maintain an overall neutral or positive charge of the probe, a positively charged Cy5 dye was used as a label, and added lysines on either ends to improve solubility. The choice of a cationic fluorophore is also important in ensuring that any free dye remaining form the synthesis process will not focus under ITP. A dye with an emission spectrum at longer wavelengths (peak at 670 nm) was chosen, since there is typically less background fluorescence at these wavelengths, and higher signal to noise ratio can be obtained.

To demonstrate focusing of shorter targets a 17-mer TAMRA-labeled PNA probe was used, without an addition of lysines on its residues, TAMRA-OO-ATTCGTTG-GAAACGGGA (SEQ ID NO: 1), synthesized by BioSynthesis) (Lewisville, Tex.). Similar to Cy5, TAMRA is a cationic dye, expected to have a single positive charge, thus imparting an overall positive charge on the PNA probe.

The concentration of the probe was chosen while considering the tradeoff between the reaction rate (for which the concentration should be as high as possible) and the specificity of the reaction (for which the concentration should be lower than the dissociation constant of any non-specific hybridization. In all experiments a probe concentration of 10 nM was utilized, which, as shown in the results section, allows specific reaction between the probe and the target, while maintaining a relatively short reaction time of less than 15 min.

Targets

For the Cy5 probe, synthetic target DNA sequences between 30- and 200-mer in length were used, and for the TAMRA based probe synthetic targets in the range of 17- to 120-mer. All sequences were synthesized by Sigma-Aldrich (St. Louis, Mo.), and are listed in Table 1.

TABLE 1

Sequences of PNA probes and DNA targets used in the experiments

| | |
|---|---|
| Probe-I | Cy5-Lys-O-CGTCAATGAGCAAA-Lys (SEQ ID NO: 5) |
| 30-mer-I | 5'-TTAATACCTTTGCTCATTGACGTTACCCGC-3' (SEQ ID NO: 6) |
| 40-mer-I | 5'-AATACCTTTGCTCATTGACGTTACCCGCAGAAGAAGCACC-3' (SEQ ID NO: 7) |

TABLE 1-continued

Sequences of PNA probes and DNA targets used in the experiments 50-mer-I 5'-
TAAAGTTAATACCTTTGCTCATTGACGTTACCCGCAGAAGAAGCACCGG
C-3' (SEQ ID NO: 8)

60-mer-I 5'-
AGGAAGGGAGTAAAGTTAATACCTTTGCTCATTGACGTTACCCGCAGAA
GAAGCACCGGC-3' (SEQ ID NO: 9)

80-mer-I 5'-
GAGTAAAGTTAATACCTTTGCTCATTGACGTTACTTACCCGCAGAAGAA
GCACCGGCTAACTCCGTGCCAGCAGCCGCGG-3' (SEQ ID NO: 10)

100-mer-I 5'-
ACTTTCAGCGGGGAGGAAGGGAGTAAAGTTAATACC**TTTGCTCATTGAC
G**TTACTTACCCGCAGAAGAAGCACCGGCTAACTCCGTGCCAGCAGCCGC
GG-3' (SEQ ID NO: 11)

120-mer-I 5'-
AGGCCTTCGGGTTGTAAAGTACTTTCAGCGGGGAGGAAGGGAGTAAAGT
TAATACCTTTGCTCATTGACGTTACTTACCCGCAGAAGAAGCACCGGCT
AACTCCGTGCCAGCAGCCGCGG-3' (SEQ ID NO: 12)

200-mer-I 5'-
ATGCAGCCATGCCGCGTGTATGAAGAAGGCCTTCGGGTTGTAAAGTACTT
TCAGCGGGGAGGAAGGGAGTAAAGTTAATACCTTTGCTCATTGACGTTA
CTTACCCGCAGAAGAAGCACCGGCTAACTCCGTGCCAGCAGCCGCGGTA
ATACGGAGGGTGCAAGCGTTAATCGGAATTACTGGGCGTAAAGCGCACG
CAG-3' (SEQ ID NO: 13)

Probe-II TAMRA-OO-ATTCGTTGGAAACGGGA (SEQ ID NO: 1)

17-mer-II 5'-TCCCGTTTCCAACGAAT-3' (SEQ ID NO: 3)

35-mer-II 5'-TTCGACGCTTCCCGTTTCCAACGAATACTTAGGTT-3' (SEQ ID NO: 2)

78-mer-II 5'-
TTCGACGCTTCGACGCTTCGACGCTTCCCGTTTCCAACGAATACTTAGGT
TACTTAGGTTACTTAGGTTACTTAGGTT-3' (SEQ ID NO: 14)

120-mer-II 5'-
TGCATCGATACATAAAACGTCTTCGACGCTTCGACGCTTCACGCT**TCCCG
TTTCCAACGAAT**ACTTAGGTTACTTAGGTTACTTAGGTTACTTAGGTTCC
TGATTGTATCCGCATCTGAG-3'(SEQ ID NO: 15)

120-mer-
random
5'-
CTCAGAGTATATACATTCCATAGATCTGGATACCCGTCAACCTTATCGAT
CCTCACAAGATGTCTCGGTCGAATAAAGATCAGAGTATATACATTCCATA
GATCTGCATACCCGTCAACC-3' (SEQ ID NO: 16)

*Complementary sequences in the targets are underlined.

Buffers

While the PNA probes, in particular those with additional lysines, are expected to be neutral or positively charged, in practice significant focusing of free PNA probes were observed, when using an anionic ITP chemistry with a very low mobility TE. An empirically designed buffer system which focuses PNA-DNA complexes but not free (unbound) PNA probes was generated. For all experiments the LE buffer was composed of 200 mM HCl, 400 mM Bis-Tris. The TE buffer was composed of 10 mM MES and 20 mM Bis-Tris. 1% of 1.3 MDa polyvinylpyrrolidone (PVP) was used in the LE for suppression of electroosmotic flow (EOF), (39) and 30% acetonitrile in the TE to improve PNA solubility. All chemicals were obtained from Sigma-Aldrich (St. Louis, Mo.).

TABLE 2

Details of the buffer solutions used as the leading and trailing electrolytes.

| | Composition | pH Value | Effective Mobility |
|---|---|---|---|
| Leading Electrolyte | 200 mM HCl | 6.527 | $-65.83 \cdot 10^{-9}$ $[m^2V^{-1}s^{-1}]$ |
| Counter Ion | 400 mM Bis-Tris | | |
| Trailing Electrolyte | 10 mM MES | 6.809 | $-16.96 \cdot 10^{-9}$ $[m^2V^{-1}s^{-1}]$ |
| Counter Ion | 20 mM Bis-Tris | | |

*The effective mobility and pH values for the LE and TE zones are numerically calculated using SPRESSO.(40)

Assay Description

For each experiment the microfluidic channel was filled with LE, by filling the LE reservoir with 10 µl of LE and applying vacuum to the TE reservoir. 10 nM of fluorescently labeled PNA probes were mixed in TE buffer with DNA targets at concentrations between 100 fM and 10 nM. The mixture was incubated for 15 minutes at 37° C., and injected the mixture into the TE reservoir, after rinsing it with DI. A voltage of 600V was applied across the channel using a high voltage sourcemeter (2410, Keithley Instruments, Cleveland, Ohio, USA). Matlab (R2012b, Mathworks, Natick, Mass.) was used to control the PMT and the sourcemeter and record the data during the experiments. The detector was located at a distance of 18 mm from the TE reservoir. Between experiments the channel was cleaned by flowing 3.5% bleach (sodium hypochlorite) and 1M NaOH through the channel for 5 minutes each.

Sensitivity and Dynamic Range

FIG. 8a presents experimental results demonstrating the limit of detection, sensitivity and dynamic range of the assay. Despite the high initial probe concentration of 10 nM, the signal registered in the control case was similar to the signal obtained when no probes are present in the reservoir.

Two control cases were performed; in control case I no targets or probes were present in the reservoir. The signal obtained in this case is the baseline signal corresponding to the detectable inherent contamination in the buffers. In control case II, a high, 10 nM, concentration of fluorescently labeled probes was added to the TE (still with no DNA targets. The signal detected in this case is similar to control case I, confirming that the chosen ITP chemistry prevents free PNA probes from focusing at the ITP interface.

Figure 8:
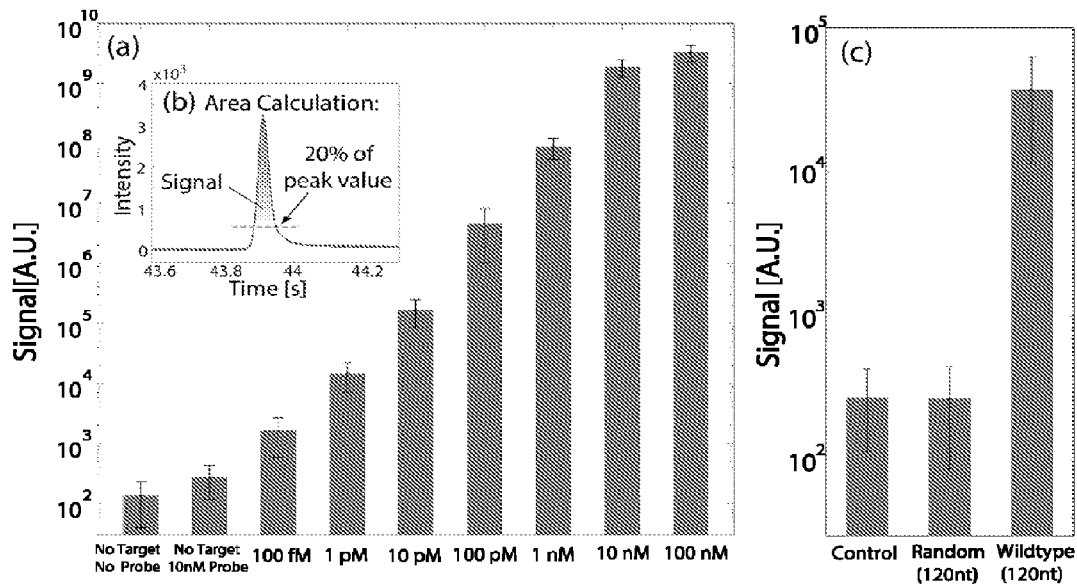
FIG. 8. Are graphs showing: (a) Experimental results showing the sensitivity and dynamic range of DNA detection using fluorescently labeled PNA probes for initial concentrations of target between 100 fM and 10 nM. Each bar represents an area average of the intensity profile of the fluorescent signal registered 18 mm from the TE reservoir. A fixed concentration of 10 nM of PNA probes was injected into the TE, and vary the range of a 200 nt DNA target between 100 fM and 10 nM. In the control case, no targets or probes are added to the reservoir. When probe is added but no targets are present the signal is not affected. The error-bars correspond to 95% confidence on the mean. The results demonstrate a dynamic range of 5 decades with a limit of detection of 100 fM. (b) The signal is calculated as the area under the curve, truncated at 20% of the peak value. (c) Specificity demonstration for complementary and random targets 120 nt in length. The control bar represents no target and 10 nM probe added to the TE. Initial concentration of targets is 10 pM.

As shown in FIG. 8, the addition of 100 fM target results in a distinguishable signal above the baseline of the control cases, and defines the limit of detection of the assay for a 200 nt long target. As the concentration of the target increased, the detected signal increased proportionally up to a concentration 10 nM, indicating that the number of PNA probes delivered to the ITP interface is indeed proportional to the number of DNA targets to which they hybridize.

This provided a quantitative measure of the target DNA concentration, with a dynamic range of 5 orders of magnitude (decades) in target concentration. At target concentrations higher than the initial 10 nM concentration of the probe, the signal saturates, indicating that the reaction is complete and there are no more probes available for the hybridization reaction.

Thus it was confirmed that the use of a higher probe concentration (e.g. 1 µM) further increases the upper bound of detectable concentrations by two orders of magnitude, without affecting the lowest detectable concentrations. The use of a higher concentration of probes also enables acceleration of reactions rates. However, specificity is significantly compromised, as such concentrations even exceed the dissociation constant of non-complementary sequences.

FIG. 8c presents experimental results verifying the specificity of the assay at room temperature using a 10 nM probe concentration. The experiments were performed using complementary and random targets at a fixed concentration of 10 pM and of the same length (120 mer), and compared those to control II (10 nM of PNA probes and no DNA). While the complementary sequence results in a signal which is two orders of magnitude higher than the control, the signal obtained for the random targets cannot be distinguished from the control.

Signal Dependence on Target Length

The sensitivity experiments in the previous section were performed using a 200 nt DNA target. However, as discussed down and below, the electrophoretic mobility of the DNA-PNA complex is expected to reduce with shorter targets lengths. This results in a threshold length below which the drag added by the PNA probe hybridized to the target is too high, and the complex mobility falls below that of the trailing ion. Characterization of this threshold, as well the dependence of the signal on target length, is important in determining the range of targets for which this assay could be applicable.

Figure 9:
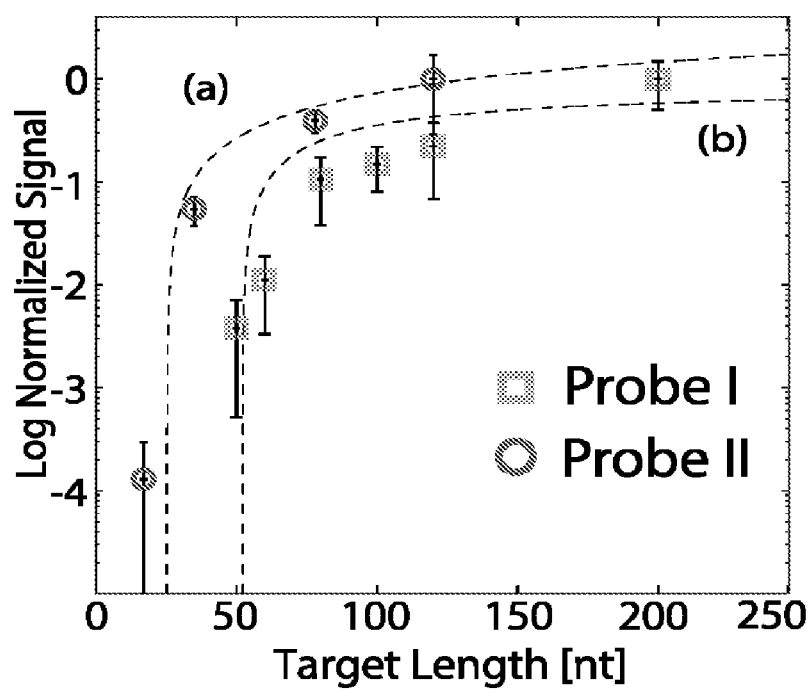
FIG. 9. Is a graph showing experimental results demonstrating detection of DNA targets between (a) 17 and 120 nt, and (b) 30 to 200 nt in length. The electrophoretic mobility of the complex increases with the length of the target, resulting in a higher influx into the ITP interface and thus higher signals for longer targets. LE is composed of 200 mM HCl and 400 mM bistris, and TE is composed of 10 mM MES and 20 mM bistris. Fixed target concentrations of 10 pM for targets complementary to probe I and 10 nM for targets complementary to probe II (see table 1) were mixed with the TE, and a voltage of 600V was applied across the 35 mm channel. Probe II does not contain (positively charged) lysine groups and thus affects less the mobility of the target, resulting in a lower threshold of detectable target lengths (17 nt(BP) and/or 35 nt) compared to probe I (50 nt). Dashed lines represent fitted curves according to the model presented herein.

FIG. 9 presents the signal obtained in ITP, as a function of the length of the target, for the two probes. In all experiments, the target concentration is 10 pM, regardless of its length. As expected, the electrophoretic mobility of the complex increases with the length of the target, resulting in a higher influx into the ITP interface and thus higher signals for longer targets. Importantly, it was shown that the assay was able to detect sequences as short as 50 nt using probe I, and 35 nt and/or 17 nt for probe II. This difference in the detectable target length thresholds was attributed to the additional lysine groups present in Probe I. While this chemical modification improves the solubility of the probe, it also adds significant drag and lowers the overall complex mobility.

Example 3

Choice of TE

In peak mode ITP with sample mixed in the TE reservoir, the amount of accumulated sample at the ITP interface, $N_a$, is determined by the ratio of the electrophoretic mobility of the analyte, $\mu_a$, and of the TE, $\mu_{TE}$, $$N_a \sim \frac{\mu_a}{\mu_{TE}} - 1.$$

Tricine with bistris was used as counterion in the TE buffer in a typical ITP assay, yielding a mobility of $5.68 \cdot 10^{-9}$ $[m^2V^{-1}s^{-1}]$, which is typically lower than analytes of interest (e.g. DNA has a typical mobility of $32 \times 10^9 - 38 \times 10^9$ $[m^2V^{-1}s^{-1}]$).

In an ideal case, the PNA probes would have a neutral charge, and thus would not focus under any ITP chemistry. In such a case, even an extremely low mobility TE would not focus the free PNA, but would indeed focus the charged DNA-PNA hybrid. However, in practice, across several PNA designs from different vendors, it was observed that the PNA probes have a net negative charge. This is despite the fact that these PNA molecules were also labeled with a cationic (i.e. positively charged) dye.

Therefore, selective focusing of PNA-DNA complexes, but not free PNA required specific choice of an ITP system comprised of a TE buffer with sufficient mobility to overspeed the free PNA probes but not the PNA-DNA complexes. This condition is summarized as follows:

$$\mu_{PNA} < \mu_{TE} < \mu_{complex}.$$

Figure 5:
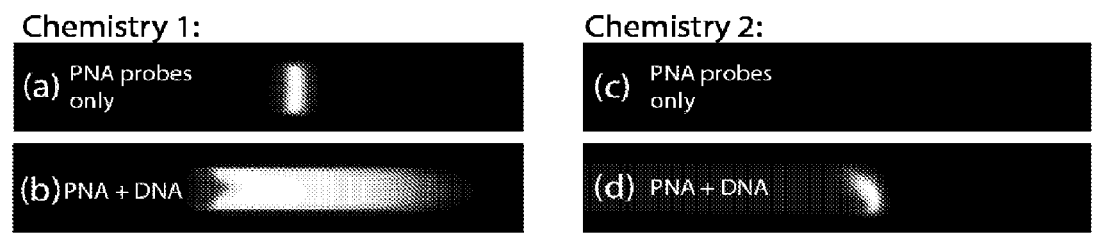
FIG. 5. Is a micrograph of raw fluorescence images showing the ITP interface for the following initial contents in the TE reservoir: (a) 1 µM PNA mixed in 10 mM tricine and 20 mM bistris. (b) 1 µM DNA and 1 µM PNA mixed in 10 mM tricine and 20 mM bistris. (c) 1 µM PNA mixed in 10 mM MES and 20 mM bistris. (d) 1 µM DNA and 1 µM PNA mixed in 10 mM MES and 20 mM bistris. In all cases LE is 200 mM HCl and 400 mM bistris. All experiments were conducted at constant voltage of 400 Volt. Chemistry 1 (tricine-based) results in a TE mobility which is too low and which focuses both the free and the hybridized PNA-probes. This is equivalent to false positives, as signal is obtained even in the absence of a target. In contrast, chemistry 2 (MES-based) results in a TE mobility which is sufficiently low to significantly focus the PNA-DNA hybrids, yet sufficiently high to reject the free PNA probes.

The effect of the choice of TE on the functionality of the assay is provided in FIG. 5. When a standard low mobility TE chemistry (based on tricine-bistris) was utilized a significant signal was even obtained when no DNA targets were present. This is because the TE mobility is even slower than the free PNA probes.

In contrast, when the specifically designed ITP chemistry (based on MES-bistris) was utilized, no signal for the free PNA probes was essentially obtained, while maintaining a significant signal when DNA targets are present. The exact ITP composition for each of the cases is provided in Table 3.

TABLE 3

Summary of the TE buffer compositions used in the experiments presented in FIG. 1. The effective mobility and pH values for each TE zone are numerically calculated using SPRESSO, for LE consisting of 200 mM HCl and 400 mM bistris.

| TE Composition | pH Value | Effective Mobility |
|---|---|---|
| 10 mM Tricine 20 mM Bistris | 7.51 | $-5.66 \cdot 10^{-9}$ [m$^2$V$^{-1}$s$^{-1}$] |
| 10 mM MES 20 mM Bistris | 6.81 | $-16.96 \cdot 10^{-9}$ [m$^2$V$^{-1}$s$^{-1}$] |

Example 4

Cationic Label

The fluorescent label affected the charge and therefore the effective mobility of the probe. In addition, probes solution was often contaminated with a low concentration of free dye (either residual dye from the synthesis, or due to dye molecules detached from the probes). Negatively charged dyes both increased the mobility of the PNA probe to which they were attached, and focused under ITP, causing false signal. Hence the use of a cationic dye as a label was found to be essential for the present invention. When a cationic dye was utilized, even if free dye molecules were present, focusing was not observed. This enabled the detection of signal only in case of focused PNA-DNA complexes.

Example 5

Model Prediction

Consider a single stranded DNA target of length $L_D$ (measured in number of nucleotides) to which a PNA probe of length $L_P$ is hybridized. The unhybridized section of the DNA was denoted as L, where $L=L_D-L_P$. Using a similar approach to Savard et al., the PNA-DNA conjugate was modeled as a single-stranded DNA with a non-zero mobility drag-tag. The mobility of the complex was modeled as the sum of two contributions: the single stranded DNA section and the drag-tag section, $$\mu = \mu_D \frac{L}{L+\alpha} + \mu_{PD} \frac{\alpha}{L+\alpha},$$

where $\mu_D$ and $\mu_{PD}$ are respectively the mobility of the DNA and PNA-DNA hybrid in free solution, and $\alpha$ is the effective friction coefficient representing the ratio of the friction coefficient of the drag-tag to that of a single DNA monomer.

Both theory and experiments confirmed that the total mobility of a DNA molecule in free solution is essentially independent on DNA size and equal to the mobility of a single DNA monomer. An estimate of $\mu_D=38\times10^{-9}$ [m$^2$V$^{-1}$s$^{-1}$], based on measurements of Stellwagen et al. was utilized. Based on measurements according to the present invention it was estimated that the mobility of the 17 nt long PNA probe as $16\times10^{-9}$ [m$^2$V$^{-1}$s$^{-1}$], and assume it is roughly independent of pH.

Figure 6:
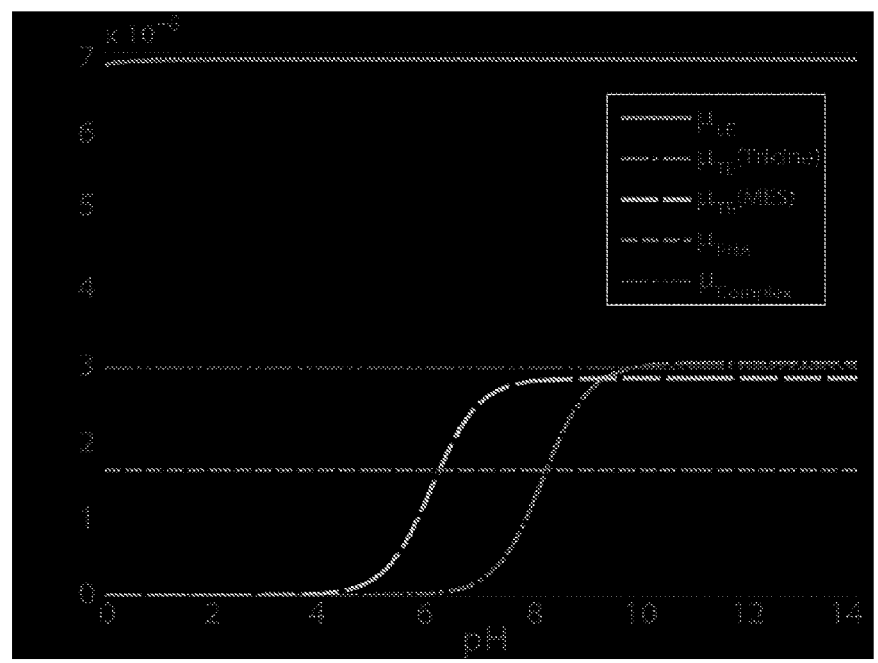
FIG. 6. Is a graph demonstrating an assay design based on model predictions, for LE consisting of 200 mM HCl and 400 mM bistris, and two different chemistries of TE: chemistry 1 consisting of 10 mM tricine and 20 mM bistris and chemistry 2 consisting of 10 mM MES and 20 mM bistris. A PNA mobility of $16 \times 10^{-9}$ $[m^2V^{-1}s^{-1}]$ was used, and a complex mobility calculated for a 120 nt target. Vertical dashed lines represent the interception point of the PNA mobility and TE mobility. The mobility of the TE in chemistry 1 is lower than both free PNA and the complex for pH<8.2. In contrast, the TE mobility in chemistry 2 is higher than that of the PNA but lower than that of the complex in the range of pH >6.2 enabling focusing the PNA-DNA complexes, while preventing the focusing of free PNA probes. Thus, only chemistry 2 is efficient in the range of 6.2<pH<8.2.

FIG. 6 presents the use of the model for design of an appropriate ITP chemistry for detection of a 120 long DNA target, using a 17 nt PNA probe. The mobilities of an HCl leading ion were calculated, and two trailing ions (tricine and MES), as a function of pH. Proper working conditions were determined such that the mobility of the PNA-DNA complex was bracketed between those of the LE and TE, and yet, the free PNA mobility was lower than that of the TE, $\mu_{PNA}<\mu_{TE}<\mu_{complex}<\mu_{LE}$.

Clearly, for both trailing ions, and across all pH values, the condition $\mu_{TE}<\mu_{complex}<\mu_{LE}$ was fully satisfied. However, requiring the pH to be between 6-8 (typical physiological working pH), it was observed that while the PNA mobility is indeed lower than that of MES (satisfying $\mu_{PNA}<\mu_{TE}$), it was in fact higher than that of tricine. These results were in full agreement with the observations provided herein.

Figure 7:
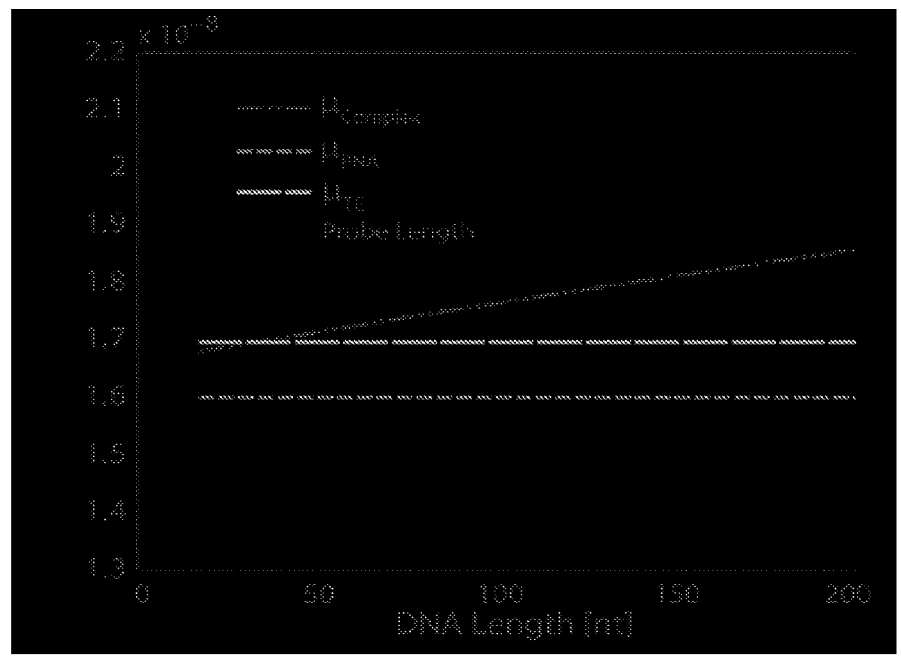
FIG. 7. Is a graph providing the model prediction for mobility dependence on target length, for LE consisting of 200 mM HCl and 400 mM bistris, TE consisting of 10 mM MES and 20 mM bistris, and PNA probe length of 17 [nt]. For short targets, the electrophoretic mobility of the complex is lower than that of the TE, but as the length of the target increases, so does the electrophoretic mobility of the complex. When the electrophoretic mobility of the unhybridized section of the DNA target overcomes the drag added by the PNA probe, the mobility of the complex exceeds the mobility of the TE, leading to focusing of the complexes. An effective friction coefficient of $\alpha=2000$ was utilized, a complex mobility of $\mu_{PD}=16.8 \times 10^{-9}$ $[m^2V^{-1}s^{-1}]$, and a DNA mobility of $\mu_D=38 \times 10^{-9}$ $[m^2V^{-1}s^{-1}]$.

FIG. 7 presents a different aspect of the same model, which allows predicting the length of targets that could be focused, for a given ITP chemistry. For short targets, the electrophoretic mobility of the complex was lower than that of the TE, but as the length of the target increases, so does the electrophoretic mobility of the complex, according to the below equation. Focusing occurred when the mobility of the complex was higher than the mobility of the TE. The threshold length is thus given by $$L_b = \alpha \frac{\mu_{PD} - \mu_{TE}}{\mu_{TE} - \mu_D} + L_P.$$

The invention claimed is:

1. A method for sequence-specifically detecting a nucleic acid molecule, comprising the consecutive steps of:
   a. contacting in an absence of an electric field, a mixture of nucleic acid molecules with a base pairing hybridizing molecule (BPHM) having a sequence of interest in a first solution and obtaining a hybrid consisting said nucleic acid molecule and said BPHM;
   b. introducing said first solution comprising said hybrid resulting from step (a) into an ITP system, said ITP system comprises a second solution of high effective mobility leading electrolyte (LE) ions and a third solution of low effective mobility trailing electrolyte (TE);
   c. applying said electric field across said second solution and said third solution; wherein said hybrid but not free BPHM focus at the sharp LE-TE interface in said ITP system, wherein said TE has a higher mobility than the BPHM and said TE has a lower mobility than said hybrid, thereby sequence-specifically said detecting said nucleic acid molecule by a signal from a label.

2. The method of claim 1, further comprising a counter-flow for holding said LE-TE interface stationary.

3. The method of claim 1, wherein BPHM comprises a positively charged marker; or wherein said labeled BPHM further comprises a positively charged label.

4. The method of claim 1, wherein said detecting is achieved by using a device selected from the group consisting of: a photodetector, a photomultiplier tube (PMT), a conductivity detector, a radioactive detector, and a camera.

5. The method of claim 3, wherein said positively charged marker is labeled with a cationic marker.

6. The method of claim 1, wherein said BPHM is selected from the group consisting of: fluorescently labeled, chemiluminescently labeled, radioactively labeled, or calorimetrically labeled.

7. The method of claim 1, wherein said nucleic acid molecule within said hybrid comprises 10 or more nucleotides.

8. The method of claim 1, wherein said first solution comprises TE.

9. The method of claim 1, wherein said free BPHM does not focus under ITP unless hybridized to said nucleic acid molecule.

10. The method of claim 1, wherein said nucleic acid molecule is a DNA or a RNA.

11. The method of claim 1, wherein said LE comprises: HCl, or 2,2-Bis(hydroxymethyl)-2,2',2"-nitrilotriethanol.

12. The method of claim 1, wherein said TE comprises a 2-(N-morpholino)ethanesulfonic acid.

13. A method for sequence-specifically detecting a first and a second nucleic acid molecules, comprising the consecutive steps of:
   a. contacting in an absence of an electric field, a mixture of nucleic acid molecules with a first BPHM and a second BPHM in a first solution and obtaining a first hybrid and a second hybrid, wherein said first hybrid consists said first nucleic acid molecule and said first BPHM, wherein said second hybrid consists said second nucleic acid molecule and said second BPHM, wherein said first BPHM is labeled with a first label and said second BPHM is labeled with a second label said first label and said second label are different and are selected from the group consisting of: a radioactive dye, a radioisotope, a fluorescent dye, a chemiluminescent dye or a calorimetric dye;

b. introducing said first solution comprising said hybrids resulting from step (a) into an ITP system, said ITP system comprises a second solution of high effective mobility leading electrolyte (LE) ions and a third solution of low effective mobility trailing electrolyte (TE);

c. applying said electric field across said second solution and said third solution; wherein said first hybrid and said second hybrid but not a free BPHM focus at the sharp LE-TE interface in said ITP system, wherein said TE has a higher mobility than said first BPHM and said second BPHM and said TE has a lower mobility than said first hybrid and said second hybrid, thereby sequence-specifically said detecting said first and said second nucleic acid molecules by a first signal from said first label and a second signal from said second label.

14. A system comprising:
(A) a base pairing hybridizing molecule (BPHM) having a sequence of interest;
(B) a DNA molecule or a RNA molecule; and
(C) an Isotachophoresis (ITP) system, said ITP system comprises:
   (a) a first zone comprising a solution of high effective mobility leading electrolyte (LE) ions;
   (b) a second zone comprising a solution of low effective mobility trailing electrolyte (TE) ions; and
   (c) an anode and a cathode,
wherein the system is capable of performing the method of claim 1.

15. The system of claim 14, wherein said BPHM is fluorescently labeled, chemiluminescently labeled, radioactively labeled, or colorimetrically labeled.

16. The system of claim 14, wherein said TE comprises MES(2-(N-morpholino)ethanesulfonic acid).

17. The system of claim 14, wherein said LE comprises: HCl, or 2,2-Bis(hydroxymethyl)-2,2',2"-nitrilotriethanol.

18. The system of claim 14, further comprising a photodetector, a photomultiplier tube (PMT), a conductivity detector, a radioactive detector, or a camera.

19. A kit comprising a BPHM having a sequence of interest, a solution for selectively hybridizing a nucleic acid molecule and said BPHM; a solution having high effective mobility leading electrolyte (LE); a solution having low effective mobility trailing electrolyte (TE); and instructions for separating and/or detecting a hybrid consisting said nucleic acid molecule and said BPHM, wherein said TE has a higher mobility than the BPHM and said TE has a lower mobility than the nucleic acid molecule/BPHM hybrid, wherein said kit is for performing the method of claim 1.

20. A system comprising:
(A) at least two BPHMs having a sequence of interest;
(B) a plurality of DNA or RNA molecules; and
(C) an Isotachophoresis (ITP) system, said ITP system comprises:
   (a) a first zone comprising a solution of high effective mobility leading electrolyte (LE) ions;
   (b) a second zone comprising a solution of low effective mobility trailing electrolyte (TE) ions; and
   (c) an anode and a cathode,
wherein the system is capable of performing the method of claim 13.

21. A kit comprising at least two BPHMs each having a sequence of interest, a solution for selectively hybridizing a nucleic acid molecule and said BPHM; a solution having high effective mobility leading electrolyte (LE); a solution having low effective mobility trailing electrolyte (TE); and instructions for separating and/or detecting a hybrid consisting said nucleic acid molecule and said BPHM, wherein said TE has a higher mobility than the BPHM and said TE has a lower mobility than the nucleic acid molecule/BPHM hybrid, wherein said kit is for performing the method of claim 13.

* * * * *

SEQUENCE LISTING

<160> NUMBER OF SEQ ID NOS: 16

<210> SEQ ID NO 1
<211> LENGTH: 17
<212> TYPE: DNA
<213> ORGANISM: Artificial Sequence
<220> FEATURE:
<223> OTHER INFORMATION: TAMRA

<400> SEQUENCE: 1
attcgttgga aacggga

<210> SEQ ID NO 2
<211> LENGTH: 35
<212> TYPE: DNA
<213> ORGANISM: Artificial Sequence

```
<220> FEATURE:
<223> OTHER INFORMATION: Target sequence

<400> SEQUENCE: 2
ttcgacgctt cccgtttcca acgaatactt aggtt                                   35

<210> SEQ ID NO 3
<211> LENGTH: 17
<212> TYPE: DNA
<213> ORGANISM: Artificial Sequence
<220> FEATURE:
<223> OTHER INFORMATION: Target sequence

<400> SEQUENCE: 3
tcccgtttcc aacgaat                                                       17

<210> SEQ ID NO 4
<211> LENGTH: 78
<212> TYPE: DNA
<213> ORGANISM: Artificial Sequence
<220> FEATURE:
<223> OTHER INFORMATION: Target sequence

<400> SEQUENCE: 4
ttcgacgctt cgacgcttcg acgcttcccg tttccaacga atacttaggt tacttaggtt        60
acttaggtta cttaggtt                                                      78

<210> SEQ ID NO 5
<211> LENGTH: 14
<212> TYPE: DNA
<213> ORGANISM: Artificial Sequence
<220> FEATURE:
<223> OTHER INFORMATION: 16S E.coli rRNA Probe

<400> SEQUENCE: 5
cgtcaatgag caaa                                                          14

<210> SEQ ID NO 6
<211> LENGTH: 30
<212> TYPE: DNA
<213> ORGANISM: Artificial Sequence
<220> FEATURE:
<223> OTHER INFORMATION: 30-mer-I Target

<400> SEQUENCE: 6
ttaatacctt tgctcattga cgttacccgc                                         30

<210> SEQ ID NO 7
<211> LENGTH: 40
<212> TYPE: DNA
<213> ORGANISM: Artificial Sequence
<220> FEATURE:
<223> OTHER INFORMATION: 40-mer-I target

<400> SEQUENCE: 7
aatacctttg ctcattgacg ttacccgcag aagaagcacc                              40

<210> SEQ ID NO 8
<211> LENGTH: 50
<212> TYPE: DNA
<213> ORGANISM: Artificial Sequence
<220> FEATURE:
<223> OTHER INFORMATION: 50-mer-I target

<400> SEQUENCE: 8
```
taaagttaat acctttgctc attgacgtta cccgcagaag aagcaccggc    50

<210> SEQ ID NO 9
<211> LENGTH: 60
<212> TYPE: DNA
<213> ORGANISM: Artificial Sequence
<220> FEATURE:
<223> OTHER INFORMATION: 60-mer-I target

<400> SEQUENCE: 9
aggaagggag taaagttaat acctttgctc attgacgtta cccgcagaag aagcaccggc    60

<210> SEQ ID NO 10
<211> LENGTH: 80
<212> TYPE: DNA
<213> ORGANISM: Artificial Sequence
<220> FEATURE:
<223> OTHER INFORMATION: 80-mer-I target

<400> SEQUENCE: 10
gagtaaagtt aatacctttg ctcattgacg ttacttaccc gcagaagaag caccggctaa    60
ctccgtgcca gcagccgcgg    80

<210> SEQ ID NO 11
<211> LENGTH: 100
<212> TYPE: DNA
<213> ORGANISM: Artificial Sequence
<220> FEATURE:
<223> OTHER INFORMATION: 100-mer-I target

<400> SEQUENCE: 11
actttcagcg gggaggaagg gagtaaagtt aatacctttg ctcattgacg ttacttaccc    60
gcagaagaag caccggctaa ctccgtgcca gcagccgcgg    100

<210> SEQ ID NO 12
<211> LENGTH: 120
<212> TYPE: DNA
<213> ORGANISM: Artificial Sequence
<220> FEATURE:
<223> OTHER INFORMATION: 120-mer-I target

<400> SEQUENCE: 12
aggccttcgg gttgtaaagt actttcagcg gggaggaagg gagtaaagtt aatacctttg    60
ctcattgacg ttacttaccc gcagaagaag caccggctaa ctccgtgcca gcagccgcgg    120

<210> SEQ ID NO 13
<211> LENGTH: 200
<212> TYPE: DNA
<213> ORGANISM: Artificial Sequence
<220> FEATURE:
<223> OTHER INFORMATION: 200-mer-I target

<400> SEQUENCE: 13
atgcagccat gccgcgtgta tgaagaaggc cttcggttg taaagtactt tcagcgggga    60
ggaagggagt aaagttaata cctttgctca ttgacgttac ttacccgcag aagaagcacc    120
ggctaactcc gtgccagcag ccgcggtaat acgagggtg caagcgttaa tcggaattac    180
tgggcgtaaa gcgcacgcag    200

<210> SEQ ID NO 14
<211> LENGTH: 78
<212> TYPE: DNA
<213> ORGANISM: Artificial Sequence

```
<220> FEATURE:
<223> OTHER INFORMATION: 78-mer-II probe

<400> SEQUENCE: 14
ttcgacgctt cgacgcttcg acgcttcccg tttccaacga atacttaggt tacttaggtt    60
acttaggtta cttaggtt                                                  78

<210> SEQ ID NO 15
<211> LENGTH: 120
<212> TYPE: DNA
<213> ORGANISM: Artificial Sequence
<220> FEATURE:
<223> OTHER INFORMATION: 120-mer-II probe

<400> SEQUENCE: 15
tgcatcgata cataaaacgt cttcgacgct tcgacgcttc acgcttcccg tttccaacga    60
atacttaggt tacttaggtt acttaggtta cttaggttcc tgattgtatc cgcatctgag   120

<210> SEQ ID NO 16
<211> LENGTH: 120
<212> TYPE: DNA
<213> ORGANISM: Artificial Sequence
<220> FEATURE:
<223> OTHER INFORMATION: 120-mer-random probe

<400> SEQUENCE: 16
ctcagagtat atacattcca tagatctgga tacccgtcaa ccttatcgat cctcacaaga    60
tgtctcggtc gaataaagat cagagtatat acattccata gatctgcata cccgtcaacc  120
```